(12) United States Patent
Ching

(10) Patent No.: US 7,551,762 B2
(45) Date of Patent: Jun. 23, 2009

(54) METHOD AND SYSTEM FOR AUTOMATIC VISION INSPECTION AND CLASSIFICATION OF MICROARRAY SLIDES

(75) Inventor: Wee Soon Ching, Singapore (SG)

(73) Assignee: Nanyang Polytechnic, Singapore (SG)

( * ) Notice: Subject to any disclaimer, the term of this patent is extended or adjusted under 35 U.S.C. 154(b) by 476 days.

(21) Appl. No.: 10/576,341

(22) PCT Filed: Oct. 8, 2004

(86) PCT No.: PCT/SG2004/000330

§ 371 (c)(1),
(2), (4) Date: Apr. 18, 2006

(87) PCT Pub. No.: WO2005/055145

PCT Pub. Date: Jun. 16, 2005

(65) Prior Publication Data
US 2007/0071300 A1  Mar. 29, 2007

(30) Foreign Application Priority Data
Dec. 8, 2003 (SG) ............................ 200307225-3

(51) Int. Cl.
G06K 9/00 (2006.01)
G01B 11/04 (2006.01)

(52) U.S. Cl. ................ 382/129; 382/168; 382/133; 382/134; 422/63; 422/68.1; 422/100; 422/105; 356/614; 356/237.1; 356/237.6

(58) Field of Classification Search ............... 382/129, 382/168, 133, 134; 422/63, 68.1, 100, 105; 73/863.01, 864.01, 864.11, 864.25; 356/614, 356/237.1, 237.6
See application file for complete search history.

(56) References Cited

U.S. PATENT DOCUMENTS

| 4,538,299 A | 8/1985 | DeForest |
| 5,220,647 A | 6/1993 | Kumagai |
| 6,243,486 B1 * | 6/2001 | Weiss ........................ 382/133 |

(Continued)

FOREIGN PATENT DOCUMENTS

WO  WO2004/017376  *  2/2004

OTHER PUBLICATIONS

Gridline: Automatic Grid Alignment in DNA Microarray Scans Peter Bajcsy.*

*Primary Examiner*—Jingge Wu
*Assistant Examiner*—Nancy Bitar
(74) *Attorney, Agent, or Firm*—Lawrence Y D Ho & Associates PTE Ltd

(57) ABSTRACT

The present invention provides a unique low cost vision inspection and classification system and methods for automatic inspection and classification of a microarray slide without manual intervention. The method first performs morphological dilation operation several times such that internal microarray spots are merged as a big connected component; then, the orientation of the merged spots, with respect to the X-axis and Y-axis is computed by computing the angle of the external boundaries of the connected component using Sobel XY operators for both edges and orientation determination, or using the moment-based algorithm for direct orientation determination; and the translational offset is determined by finding the X and Y centroids of the connected component. Moreover, the present invention provides threshold methods for classifying spots into normal spots, weak spots, missing spots, or overlapping spots.

27 Claims, 10 Drawing Sheets

U.S. PATENT DOCUMENTS

| | | |
|---|---|---|
| 6,289,126 B1 | 9/2001 | Ishisaka |
| 6,558,623 B1 * | 5/2003 | Ganz et al. .................... 422/63 |
| 6,752,182 B2 * | 6/2004 | Atkinson et al. ............ 141/130 |
| 6,902,702 B1 * | 6/2005 | Winegarden et al. ........ 422/100 |
| 7,135,667 B2 * | 11/2006 | Oldham et al. ........... 250/208.1 |
| 7,455,966 B1 * | 11/2008 | Schaudies et al. ............... 435/6 |
| 2006/0188140 A1 * | 8/2006 | Gholap et al. ................ 382/133 |

* cited by examiner

METHOD AND SYSTEM FOR AUTOMATIC VISION INSPECTION AND CLASSIFICATION OF MICROARRAY SLIDES

FIELD OF THE INVENTION

The present invention relates generally to microarray technology, and more particularly to automated inspection and classification systems for microarray slides and methods of inspection and classification using the automated inspection and classification systems.

BACKGROUND OF THE INVENTION

Microarray technology revolutionizes the ways by which genes and their functions are understood. Diverse applications of the microarray technology include profiling of gene expressions, classifying of tumors and cancers, cloning of genes, identifying of cancer genes, and discovering of therapeutic molecules.

Microarray technology employs microarray slides to assay hundreds and thousands of interested targets simultaneously. For the instance of gene expression profiling, a microarray slide contains arrays of immobilized DNA samples, often called spots. The spots are usually probed by two dye-tagged or radioactively labelled cDNAs. These cDNAs are made by reverse transcription of mRNAs from biological samples of interest, such as cells from patients, cells or organisms subjected to different stresses, or cells or organisms at varying developmental stages. Following the hybridisation step, the DNA arrays are scanned to generate an array image showing the fluorescence or radioactive intensity of each spot. The fluorescence or radioactive intensity is assumed to correlate with the expression level of each gene represented by a corresponding spot. Therefore, processing of an array image of a single slide can generate expression data of a large number of genes.

However, the task of translating an image of spots with varying intensities into a table linking intensity values to each gene has been impeded by microarray technology challenges. For example, the shape, size and location of spots fluctuate significantly across an array. These fluctuations may be caused by many factors such as printing, hybridisation, and slide-surface chemistry factors, and can significantly affect the interpretation of an array image. Actually, a small manufacturing defect in the same batch of arrays could affect the data analysis of specific genes.

For minimizing the printing variations, a known way is to have on-line inspection on printing quality and then, tune the printing parameters until the best print is obtained. U.S. Pat. No. 6,558,623. Unfortunately, even best printing-parameters are subjected to variations of print tips, environmental factors, and the like. The parameters need to be tuned from time to time. Moreover, for existing systems, best printing actually means that the printing parameters are within certain tolerance, so that there will be variations among spots, even for the best printed slides. In addition, random errors do occur, introducing extra variations into spots.

Another challenge for microarray technology is that it needs to process and analyse numerous images where a single image may contain thousands of spots. As discussed above, an image of a microarray slide may not be in its perfect orientation. Thus, prior to any correlation of two or more images, the images must have the same orientation, and spots on the images must have the same alignment. One way of alignment of arrays in one image is to use grids. Sophisticated machine vision algorithms have been implemented in various software packages to help selection of grids with high precision. In most cases, the user will identify the bounding area of a sub-grid by selecting corner spots. Kuklin, A. Using array image analysis to combat HTS bottlenecks, Genetic Eng. News, 19(19): 32 (1999). The number of columns and rows enclosed in the rectangle should match the expected number of rows and columns of spots in the array, which is known a priori.

The next step is to identify the location of the corner spots of the bounding sub-grids in the image. Then, the spot-finding algorithm uses that information to create the grid. It adjusts the location of the grid points and lines to locate the arrayed spots in the image. The software should allow for additional, quick manual adjustment of the grid points if the automatic spot finding method has not been identified certain spot positions.

After positioning of the grids and identifying of the spot location and size, the software will process both control and sample images. Image segmentation algorithms are used to appropriately identify and segregate the pixels associated with each spot signal area from its local background and possible other contaminations—even if the contamination has landed on the spot.

This approach involves human intervention in the process of spot location. The procedure becomes cumbersome when hundreds of microarray images need to be processed, as is the case in high-throughput screening. A single lab could produce from a few to thousands of array images per week. Any approach involving even the smallest human efforts per spot is certainly impractical at this scale.

Therefore, it is desirable to have an automated system that needs only input of the microarray configuration (e.g., number of rows and columns of spots) and a list of image files to process, after which analysis should be performed automatically. This system should be able to search the image for grid position, identify the layout of the array, localize the spots, and perform measurements without the need of user's intervention. The goals of complete automation in microarray image processing are to provide high accuracy in spot location, eliminate noise signals from the data analysis process, and minimize operator involvement in the procedure. This approach reduces time for personnel training and operator involvement. Automation ensures consistent, high quality control of data extraction.

However, microarray slides and fully automated microarray slide machine with vision inspection capability are expensive. The present invention provides a low cost and effective automated inspection system that can run on a personal computer for the quality control of microarray slides. In addition, the present invention enables a user to use microarray slides that are only partially well printed, so that more saving is provided. Other advantages of this invention will be apparent with reference to the detailed description.

SUMMARY OF THE INVENTION

The present invention provides a unique low cost vision inspection and classification system and methods for automatic inspection and classification of a microarray slide without manual intervention. More specifically, the present invention provides an automated vision inspection and classification system that, in one preferred embodiment, includes a processing unit, an image capture unit, a control means and a slide holding and transporting means, wherein the processing unit contains application programs that are used to execute the inspection and classification of the microarray slides.

In one embodiment, the present invention provides a method of automatic inspection of a microarray slide, where the method first performs morphological dilation operation several times such that internal microarray spots are merged as a big connected component; then, the orientation of the merged spots, with respect to the X-axis and Y-axis is computed by computing the angle of the external boundaries of the connected component using Sobel XY operators for both edges and orientation determination, or using the moment-based algorithm for direct orientation determination; and the translational offset is determined by finding the X and Y centroids of the connected component. Moreover, the present invention provides threshold methods for classifying spots into normal spots, weak spots, missing spots, or overlapping spots.

Accordingly, one object of the present invention is to provide an inspection and classification system and method that inspect microarray slides automatically without user's intervention.

The objects and advantages of the present invention will become apparent from the following detailed description of preferred embodiments thereof in connection with the accompanying drawings.

BRIEF DESCRIPTION OF DRAWINGS

Preferred embodiments according to the present invention will be described with reference to the FIGs, in which like reference numerals denote like elements.

DETAILED DESCRIPTION OF THE INVENTION

Unless defined otherwise, all technical and scientific terms used herein have the same meaning as commonly understood by one of ordinary skill in the art to which this invention belongs.

Throughout this application, where publications are referenced, the disclosures of these publications are hereby incorporated by reference, in their entireties, into this application in order to more fully describe the state of art to which this invention pertains.

Figure 1:
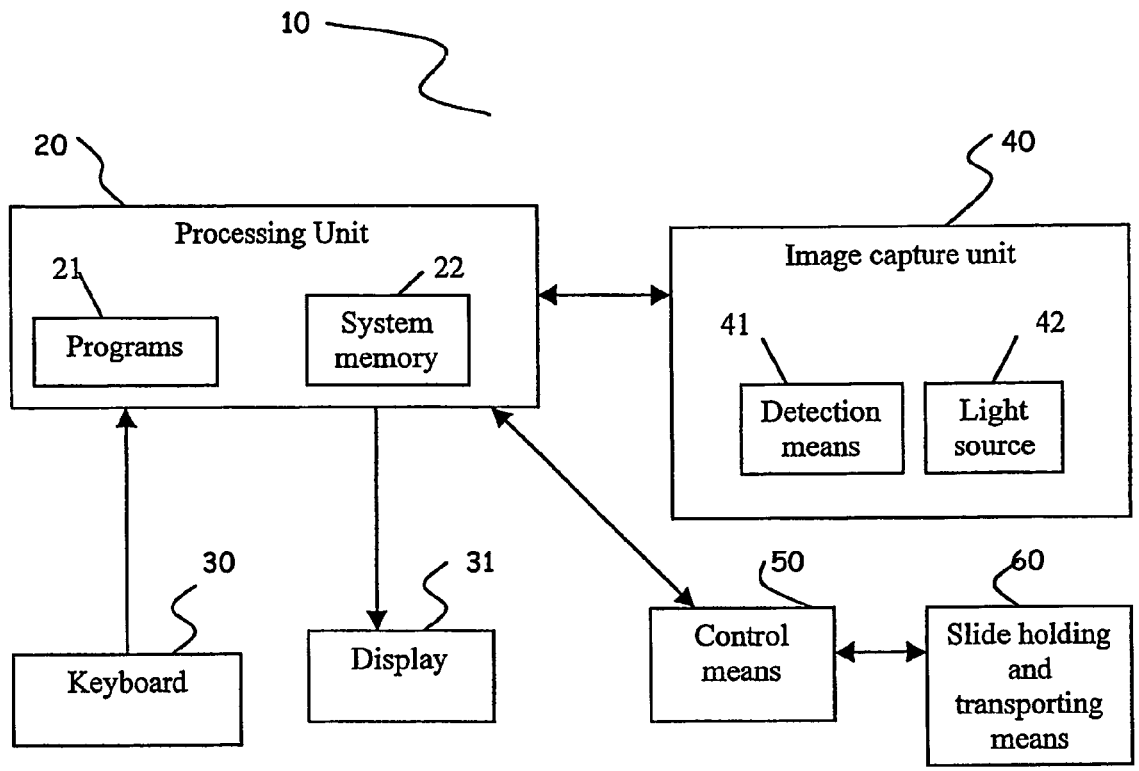
FIG. 1 shows the major components of a preferred embodiment of the automated inspection and classification system in accordance with the present invention.

Referring to FIG. 1, an image-based vision inspection and classification system 10 includes a processing unit 20, a keyboard 30, a display 31, an image capture unit 40, a control means 50, and a slide holding and transporting means 60. The processing unit 20 is electrically connected to the keyboard 30, the display 31, the image capture unit 40, and the control means 50 via separate bus lines. The processing unit 20 includes application programs 21 that are used to execute the vision inspection and classification, and a system memory 22 that includes memory space for storing the application programs 21, and initial, intermediate and finished data from execution of the application programs of the vision inspection and classification, where the data include gray scale image data, binary image data, dilated image data, offset data, and data of spot qualities. The application programs 21 and their execution in accordance with the present invention will be discussed in detail later. Preferably, the processing unit 20 is a microcomputer, and the system memory is a random access type of memory. Suitable microcomputers and memories are readily available in the market place. Their structure and operation are well known and, therefore, will not be described.

The keyboard 30 and display 31 can be any commercial products that are suitable for instructions/data input and image/data display. Therefore, they will not be described in detail herein.

The image capture unit 40 includes a detection means 41 and a light source 42. The image which is an object of processing can be obtained by optically capturing the object with a camera or the like. The detection means 41 to be used is not specifically limited as long as it is capable of converting the captured image of the object into an electric signal for output, so that it can be a charge-coupled device (CCD), a charge injection device, a photodiode array or a scanner. In one preferred embodiment, the detection means 41 is a CCD camera. For example, the CCD camera is a progressive scan camera with a model number CV-M10BX from manufacturer JAI Coorporation. It will be apparent to those skilled in the art to utilize a different CCD camera.

In certain embodiments, an ordinary video camera is used as the camera, so that the captured image is outputted as an analogue video signal obtained by scanning a plurality of pixels. Accordingly, conversion of the analogue video signal into a digital signal represented in gray-scale (multi-valued image), conversion of the digital signal into a binary signal, conversion of the binary signal into a neighbor pixel state value, and calculation of the spot characteristics can be carried out in the processing unit 20 having a CPU, a ROM, a RAM, and an I/O port.

The light source 42 is preferably a broad spectrum bulb that is configured to output light waves over a wide range of wavelengths. Preferably, the light source 42 is optically coupled to an inspected slide. In a preferred embodiment, the light source 42 is a bulb manufactured by General Electric Corporation having the model number 9W 400 Lumen. It will be apparent to those skilled in the art to select a different high frequency light source.

Various illumination methods are suitable for the present invention. The parameters that should be considered in choosing an illumination method include positions of the light source (e.g., front or back), illumination angle, effects of DNA slides printing surface, intensity of illumination, choice of lighting types, choice of diffuser, and optical alignment. In certain embodiments, the illumination method is preferably to be directional front lighting, with a suitable intensity level for achieving the best image acquisition results. The directional front lighting setup facilitates the design of microarray slide holder and the mounting of CCD vision camera for the inspection.

Figure 2:
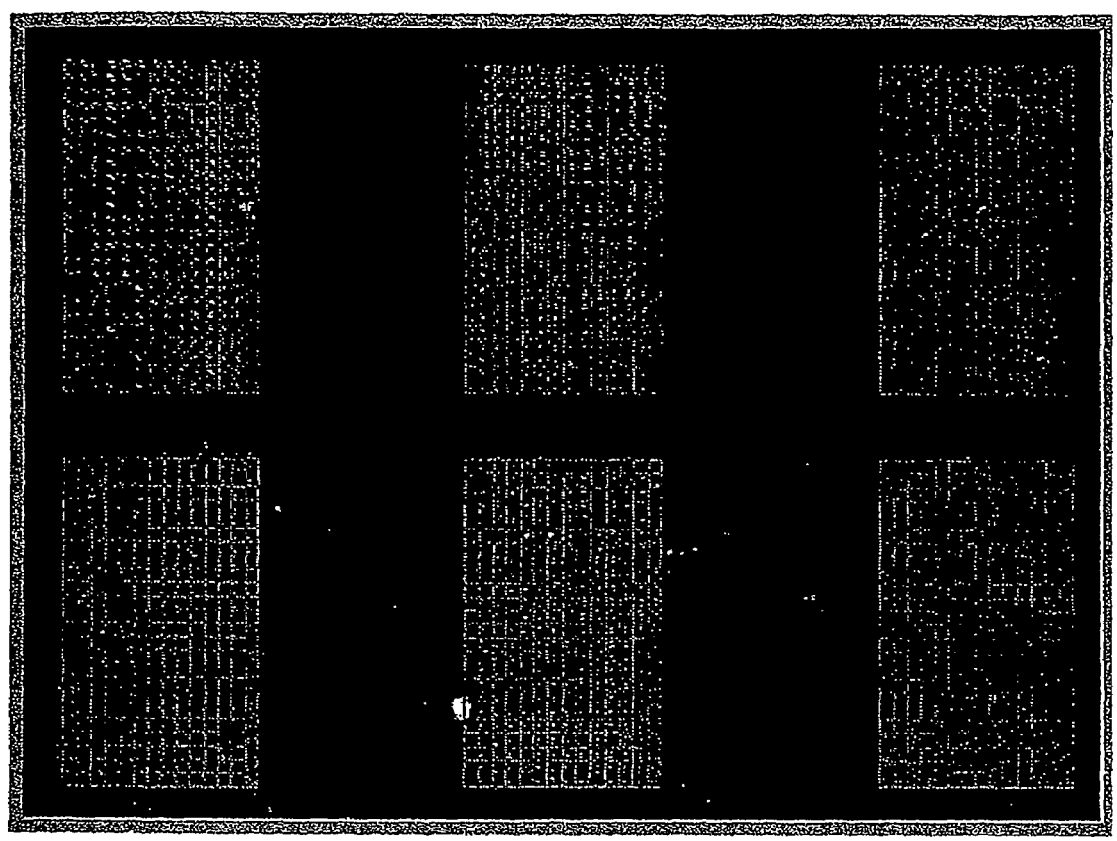
FIG. 2 shows exemplary images of cDNA slides printed on poly-L-lysine coated slides using the Virtek SDDC-2 microarrayer, wherein the images were captured by a CCD camera with a resolution of 768 by 578 pixels, and the resolution of the images was 8 bits per pixel.

The key challenge here is to be able to magnify the very small little spots on the microarray slides for the inspection by normal CCD camera without resorting to the use of microscope. By incorporating suitable optical extension tube to extend the image distance, and with a lens with a fixed focal length, the spots on the microarray slide can be clearly imaged for vision inspection. Exemplary images captured on cDNA slides are shown in FIG. 2. The cDNA slides shown were printed on poly-L-lysine coated slides using the Virtek SDDC-2 microarrayer at the National Cancer Centre of Singapore. The images were captured by a CCD camera with a resolution of 768 by 578 pixels. The resolution of the image was 8 bits per pixel.

The control means 50 receives instructions from the processing unit 20 and controls the operations of the slide holding and transporting means 60, where the processing unit 20 in turn receives signals about an inspected slide from the image capture unit 40 and processes the signals to form the instructions for the control means 50. In one preferred embodiment, the control means 50 is an SA-S5M Controller (IAI America, INC, address: 2360W, 205$^{th}$ Street, Torrance, Calif. 90501). It will be apparent to those skilled in the art to select a different control means.

The slide holding and transporting means 60 may be a linear slider including an actuator and a slide holder. The slide holder is operably disposed onto the actuator so that the slide holder can linearly slide along the actuator. An inspected slide can be loaded onto the slide holder and taken out of the slide holder either by automatic means or manually. The image of the slide can be captured by moving the slide holder with a fixed light source or by fixing the holding fixture with a moving light sources. The ways of coordinating of the movements of the light source and the holding fixture can vary in accordance with any specific application, so long as the coordination allows the capture of the image of the slide.

In certain embodiments, a controlling sub-module is built to move the pallet that holds the microarray from one position to another. A fixture is also built to hold the microarray and a linear slider is used to move the fixture with the cDNA microarray slide for automatic vision inspection. It is implemented using SEL programming language and VB6.

While the preferred embodiments of the present invention are illustrated mostly by using cDNA slides shown in FIG. 2, inventors contemplate that the inspection and classification system and method disclosed herein may be applied to any suitable microarray slides. A microarray slide may contain any of a variety of materials including, but not limited to, nucleic acids, oligonucleotides, polynucleotides, non-nucleic acid organic or inorganic chemical species, oligomers, polymers, and proteins. The microarray can also be a non-positional array or "lab-on-a-chip" system. The microarray may be supported by a glass plate, nylon film, or other equivalent support. The spot size-is not critical and can vary, preferably from 5 to 500 microns in diameter.

It is noted that microarray slides may not have proper alignment in the printing. Some may be printed too near the top edge, some may be too near the left edge, some may be slanted toward the right hand side, and so on. To tackle all these possible variations in microarray slides, the present invention provides a vision algorithm that makes use of morphological filters to detect the alignment of each slide automatically. The algorithm has greatly speeded up the automatic inspection process, and enhanced the detection accuracy.

Figure 3:
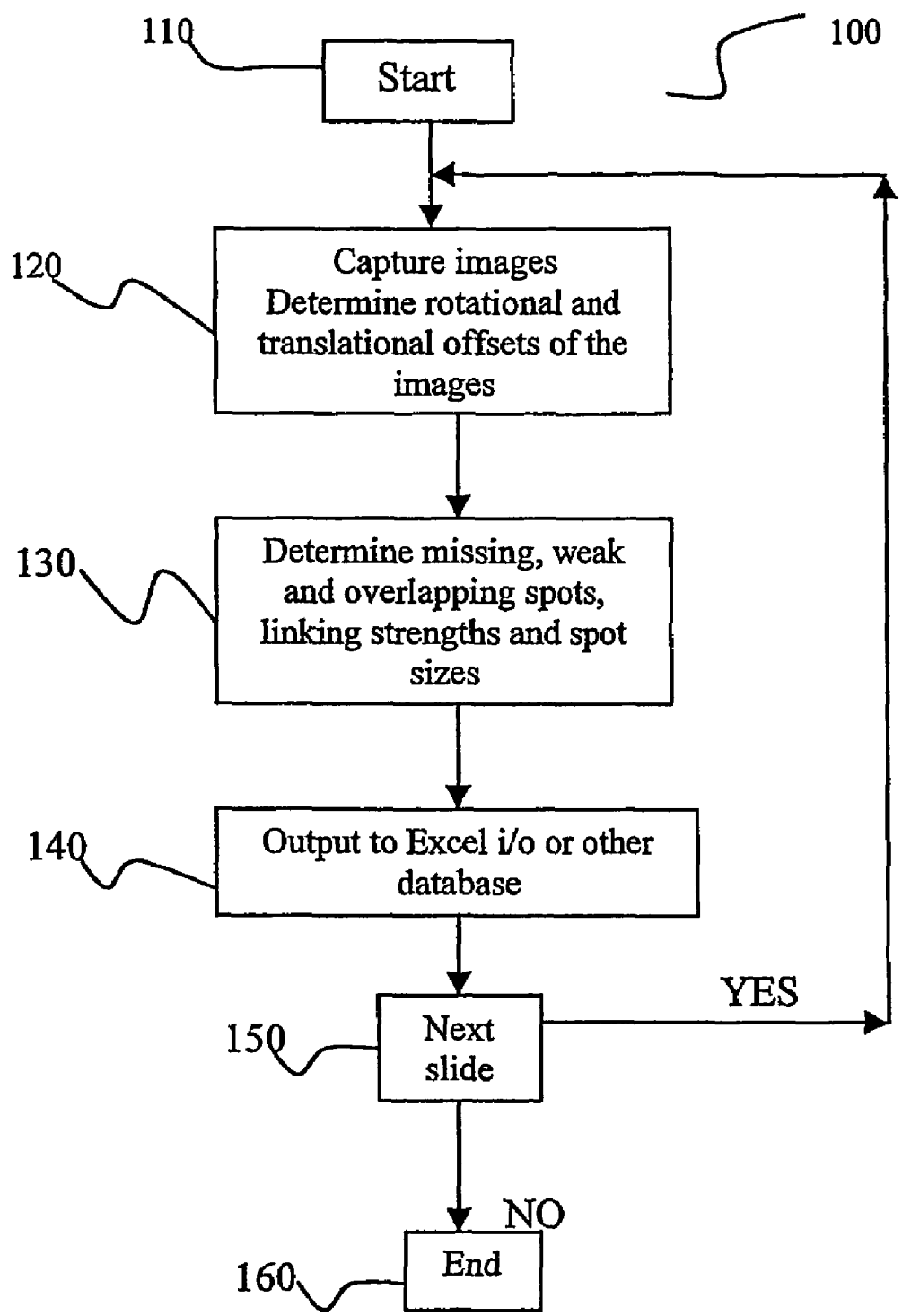
FIG. 3 shows an overall flowchart of one preferred method for automated vision inspection and classification of microarray slides.

Now referring to FIG. 3, one preferred method for the automated vision inspection and classification of microarray slides is provided in the overall flowchart. The automated vision inspection and classification method 100 includes steps of starting the system, capturing the images of slides, normalizing the images by computing rotational and translational offsets, determining the quality of spots on the slide, and outputting the processed data to be stored. Details of each step are described in detail below by using a cDNA microarray slide as an example.

For vision inspection, a cDNA microarray slide is loaded onto the actuator of the slide holding and transporting means 60. It is appreciated that, while the slides can be manually loaded, an automatic loading means will also be suitable as long as be capable of delivering the slides to the vision field of the image capture unit 40. Many automatic loading means for delivering slides are known to those skilled in the art and, therefore, will not be described herein.

Referring still to FIG. 3, step 110 of start includes setting up the vision inspection and classification system. The system is initiated by pressing the start button on the user interface on the display 31 so as to run the vision programs from the processing unit 20. During the system setup phase, the user interface provides the selection of slide type, threshold methods, and calibration procedures. The linear slider will then move the actuator so that the cDNA slide is moved to a position where the slide is under the CCD camera.

Figure 4:
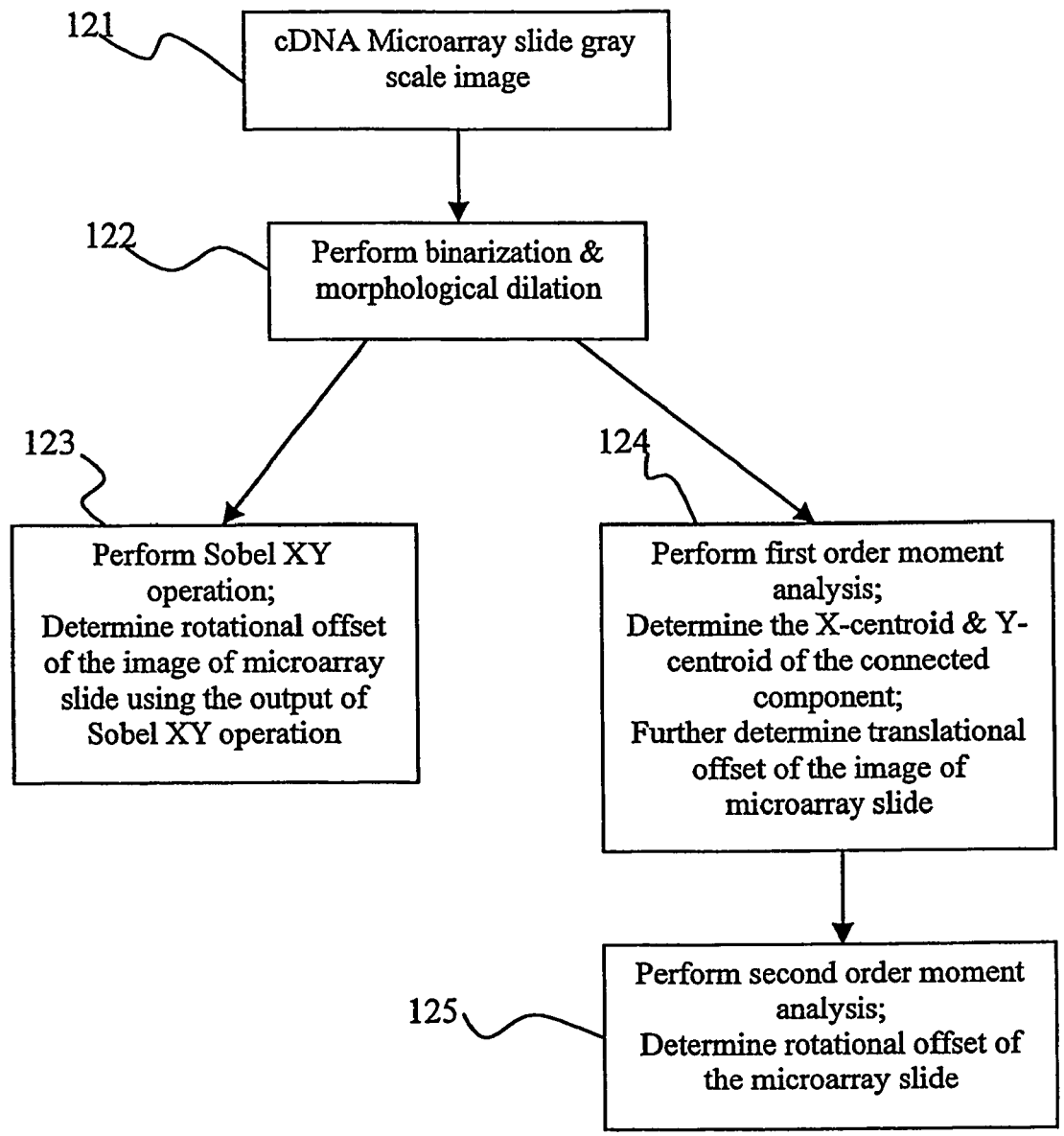
FIG. 4 shows a detailed flowchart of the steps for capturing images of cDNA microarray slides and determining of rotational and translational offsets of the captured images.

Now referring to FIG. 3 in combination with FIG. 4, there is provided a detailed description of capturing the images of slides and normalizing the images by computing the rotational and translational offsets of the images. FIG. 4 shows a detailed flowchart of the steps for capturing and normalizing the images of microarray slides. In step 121, the image of one cDNA slide will then be captured by the CCD camera, wherein the image information is stored in the system memory 22 of the processing unit 20 through the frame grabber which converts the analog image to digital image. Many algorithms are available for the function of converting the analog image to digital image. The process of capturing an image of a slide and storing the image as gray scale image data in the system memory 22 is known and, therefore, will not be described.

Microarray images consist of arrays of spots arranged in grids. All grids have the same numbers of rows and columns of spots. A microarray may have several grids, called blocks, which are arranged in relatively equal spacing with each other to form a meta-array.

The mega-array structure is an artifact of array production and is caused by using a "print-head" with multiple spotting pins. Typically, each pin of the robotic arrayer deposits DNA material in a single block.

A computer "perceives" an image as a two-dimensional array (or matrix) of numbers. Each array element is called a pixel, or picture element, and is represented in the computer as an integer value. Frequently, the pixel is represented as an unsigned 8-bit integer in the range [0, 255], with 0 corresponding to black, 255 corresponding to white, and shades of gray distributed over the middle values. However, most microarray scanners have higher than 8-bit sensitivity (closer to 12-13 bits, typically) and thus use a 16-bit TIFF format to store the images. A higher sensitivity allows for finer differentiation in the range of intensity values. A 16-bit representation produces up to 65,536 different shades of gray. Precise identification of signal pixels for microarray spots is crucial for obtaining accurate data in expression analysis.

The image stored in the system memory 22 is in gray scale. This gray scale is of 0-255 scale for the 8-bits frame grabber used. There could be other scales if different resolutions of frame grabber are used.

In step 122 of FIG. 4, the stored images are binarized, and morphologically dilated. Typically, image binarization converts a gray level image of typically 256 gray levels (intensity levels or brightness levels) to a black and white image. Many different binarization programs are known and, therefore, will not be described in detail herein. Simply put, the binarization is carried out by setting a threshold. The threshold may be set up by a variety of methods to separate spots from background. For example, if the intensity value of a pixel exceeds the threshold, the pixel will be set to white. If the intensity value of a pixel is equal to or lesser than the threshold, the pixel will be set to black. This process will greatly speed up the subsequent processing as lesser data is being used for subsequent processing and analysis work.

Figure 5A:
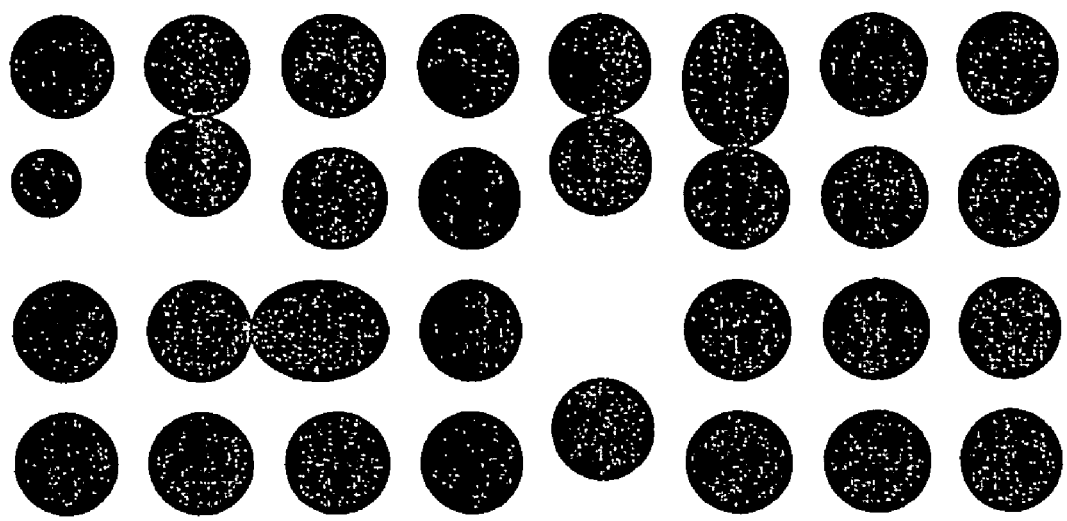
FIG. 5A is an illustration of a binarized image of one block on a cDNA slide.

The threshold selected for binarization is predetermined by computing the histogram of the image intensity histogram, which is a bi-polar image histogram. A specific threshold value will depend on slide types and be calibrated during system setup phase. In certain embodiments, the threshold intensity is preferably set up at about 150 to 180. FIG. 5A illustrates a binarized image of one block on a cDNA slide.

Figure 5B:
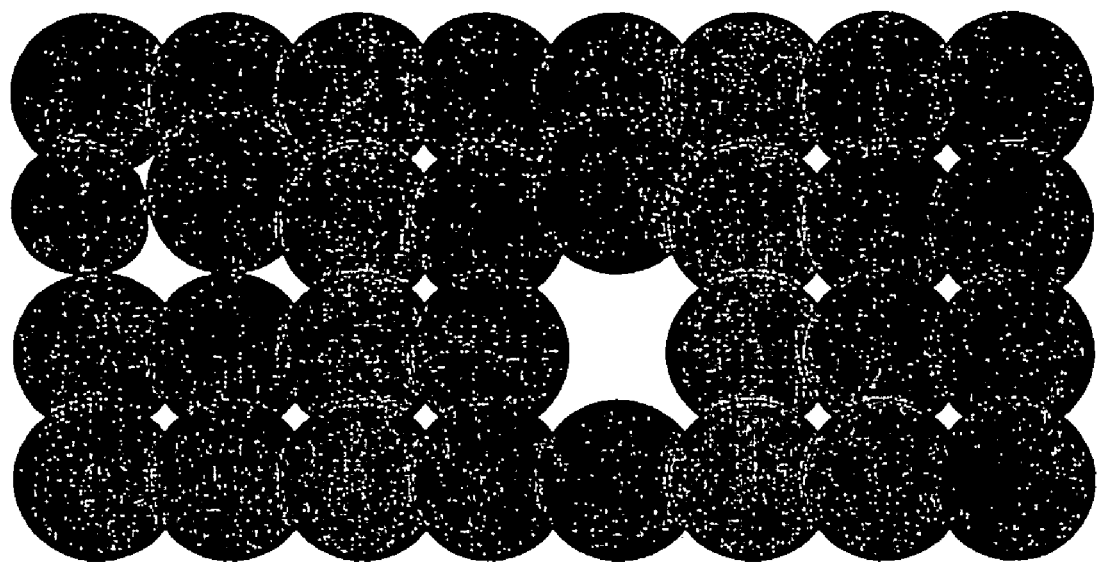
FIG. 5B shows an intermediate image during morphological dilation.
Figure 5C:
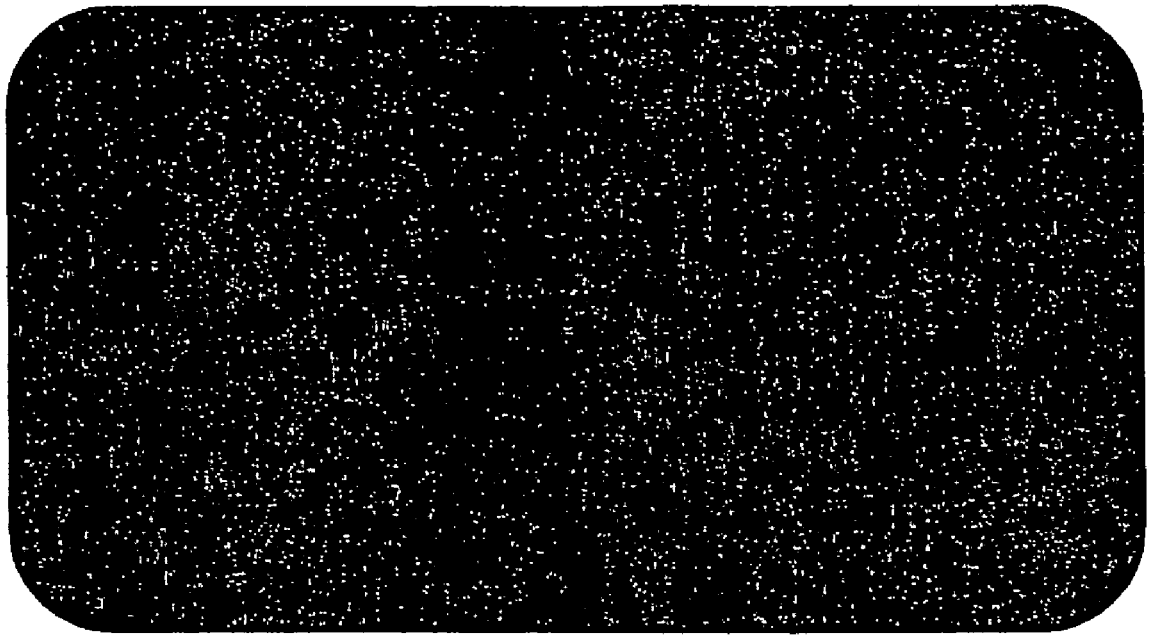
FIG. 5C shows a merged component as a result of multiple successive morphological dilation.

Referring still to step 122 of FIG. 4, a binarized image is morphologically dilated in multiple steps to merge all individual cDNA spots within the same cDNA block, as shown in FIGS. 5A, 5B and 5C. Theoretically, morphological dilation is performed to fill up the gaps between spots so that the external boundary can be detected. When morphological dilation operation is performed on a binary image, it will enlarge the image by generally one pixel and fill up small holes and gaps between components. As illustrated in FIG. 5A, there are a total of 32 cDNA microarray spots in a block. Typically, there are a total of 8 by 4 or 12 by 4 blocks in single microarray slide.

Dilation is one of the two basic operators in mathematical morphology. The basic effect of dilation on binary images is to enlarge the areas of foreground pixels at their borders. The areas of foreground pixels thus grow in size, while the background "holes" with them shrink. As an illustration, a 3×3 matrix is shown below for the morphological structuring elements (a total of 9 elements).

| 1 | 1 | 1 |
| 1 | 1 | 1 |
| 1 | 1 | 1 |

All of the structuring elements are shown as "1". The number of dilation operations is 8 for a 3×3 matrix. The dilation can be performed using the logical OR function: 1) If the pixel is set to foreground, it remains such; 2) If the pixel is set to background, but at least one of its eight neighbours is set to foreground, the pixel is converted to foreground; or 3) If the pixel is set to background and none of its eight neighbours is set to foreground, the pixel remains set to background.

It is noted that the number of morphological operation performed is dependent on the type of slide, which can be determined during the system setup phase. In the example described above, morphological transformation is conducted using a 3×3 matrix in the image. Those skilled in the art will appreciate that, though typical, such a matrix size is not necessitated by the invention, which contemplates the use of rectangular and square matrixes of other sizes as well, such as 5×5, or 7×7 matrixes.

After all spots on one block are merged into one component, a rectangle-bounding-box method is used to form a rectangle of the filled-image, FIG. 5C. In the implementation, bounding areas that are too small will be ignored, so as to differentiate the cDNA block from other noises or disturbances.

The boundary of the merged spots on one block may be determined by any conventional method. For example, U.S. Pat. No. 6,289,126 describes one conventional method for determining the boundary of one object in an image. For each object pixel in the binary image, values of the object pixel and the 8-neighbour pixels adjacent to the object pixel in the surrounding eight directions are taken out and converted by means of a look-up table into a single value, which is then stored in another frame memory. Through this step, only the pixels on the boundary of an object are allowed to have a non-zero value, and the pixels on the inside and outside of the object are allowed to have a value of "0". See also, U.S. Pat. Nos. 4,538,299 and 5,220,647.

Now referring to step 123 of FIG. 4, rotational offset of a cDNA block is calculated by using Sobel operation. While a slide has more than one block as discussed above, it is assumed that the rotational offset for each cDNA block on the same slide is the same. Thus, the description of Sobel operation for the image of one slide is represented by one block.

Rotational offset refers to the angle that a particular cDNA block makes with respect to the reference line of the respective cDNA microarray block being compared. The rotational offset is zero if the cDNA slide is printed and placed on the holder in perfect orientation.

The next step of performing Sobel XY operation will result in edges being detected, and the magnitude of the edge in the vertical direction and horizontal directions will be denoted as Gy and Gx, where Gy is determined by using Sobel Y mask of:

| −1 | −2 | −1 |
| 0 | 0 | 0 |
| 1 | 2 | 1 |

The Gx is determined by using Sobel X mask of:

| −1 | 0 | 1 |
| −2 | 0 | 2 |
| −1 | 0 | 1 |

The above edge magnitude for each image pixel is computed by computing G for each edge point by:

$G = |Gx| + |Gy|$

The orientation will be determined as:

$\tan^{-1}(Gy/Gx)$

The rotational offset is computed by getting maximum number of edge directions. Under the Sobel operation, the rotational offset value is the maximum number of edge points that give the same edge direction.

Now referring to step 124 of FIG. 4, the translational offset of one block is calculated by using 1st order moment analysis. Translational offset refers to individual block where each block has 392 spots (or other values depending on the slide type). The calculation of the translational offset is totally separated from the calculation of rotational offset by Sobel operation, except that both methods are using the same binarised, morphological dilated, and rectangle-bounded-box image.

Translational offset refers to the x and y displacement or distance with respect to a reference point, where x distance refers to the distance in horizontal direction, and y distance refers to the distance in vertical direction. The reference point is the centroid of the respective reference cDNA microarray block being compared, when the cDNA slide is printed and placed accurately on the holder.

Figure 6:
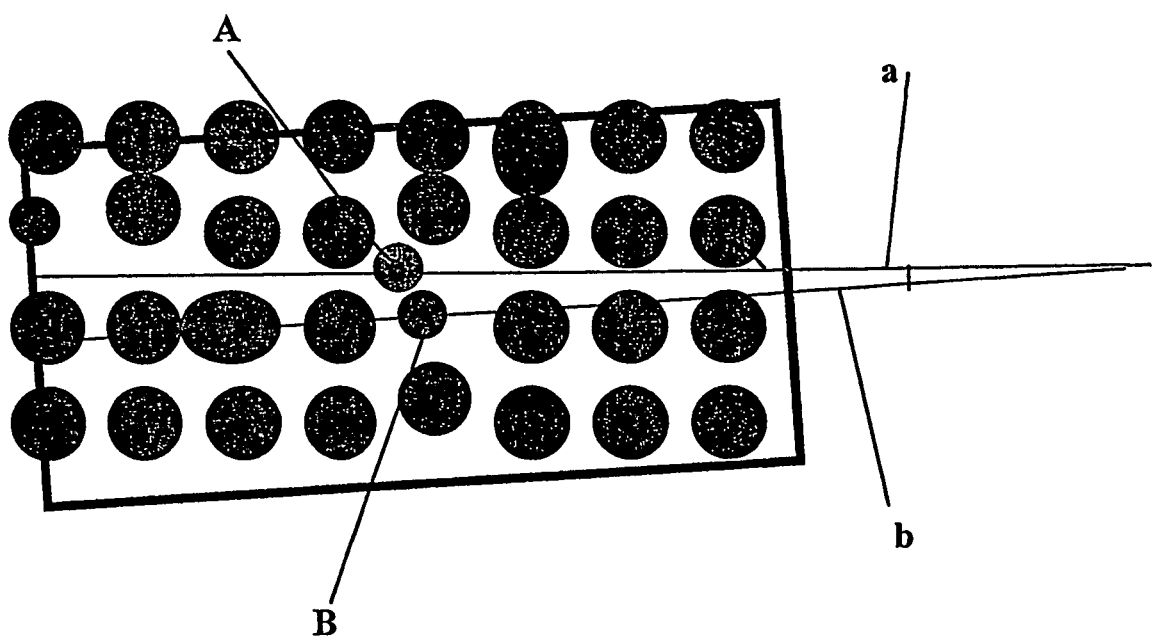
FIG. 6 illustrates the translational offset of one block on a microarray slide.

As illustrated in FIG. 6, the translational offset is the vertical and horizontal distance between the coordinate of the A dot and the B dot. The A dot denotes the centroid of the reference cDNA block in correct position. The B dot denotes the centroid of the reference CDNA block in offset position and slightly different orientation. The rotational angle is the one between the b line and the a line.

The translational offset is determined by finding the x and y centroids of the connected component through first order moment. The determination of centriod X and centroid Y will give the translational offset for the CDNA micro array slide vision inspection. The first order moment is performed on the dilated image of a cDNA block, as shown in FIG. 5C.

The general moment formulation is given in the formula below:

$$M_{ij} = \Sigma\Sigma x^i y^j P(x,y) \quad (1)$$

where i, j are the moment indices; x is the x-coordinate of the pixel, y is the y-coordinate of the pixel, and P(x,y) is the pixel's intensity.

The centroid X, denoted by Cen_X can be computed as:

$$\text{Cen}\_X = M_{1,0}/M_{0,0} \quad (2)$$

Similarly, the centroid Y, denoted as Cen_Y can be computed as:

$$\text{Cen}\_Y = M_{0,1}/M_{0,0} \quad (3)$$

Referring to step 125 of FIG. 4, the rotational offset may be calculated alternatively by using 2nd order moment. This calculation is optional because the rotational offset has been calculated by using Sobel operation as discussed above. Nevertheless, this alternative method may substantiate or verify the rotational offset obtained from the Sobel operation.

The second order moment analysis is always performed after the 1st order moment analysis to obtain the rotational offset. If only translational offset is desired, the first order moment analysis will do. The second order moment analysis is performed on the dilated image of a cDNA block, as shown in FIG. 5C.

In the calculation of rotational offset by using 2nd order moment analysis, central moment needs to be computed, as given in the formula below:

$$\mu_{ij} = \Sigma\Sigma(x-\text{Cen}\_x)^i(y-\text{Cen}\_y)^j P(x,y) \quad (4)$$

The rotational offset can then be computed based on the central moments, as follows:

$$\theta = 0.5 \tan^{-1}[2\mu_{11}/(\mu_{20}-\mu_{02})] \quad (5)$$

Figure 7:
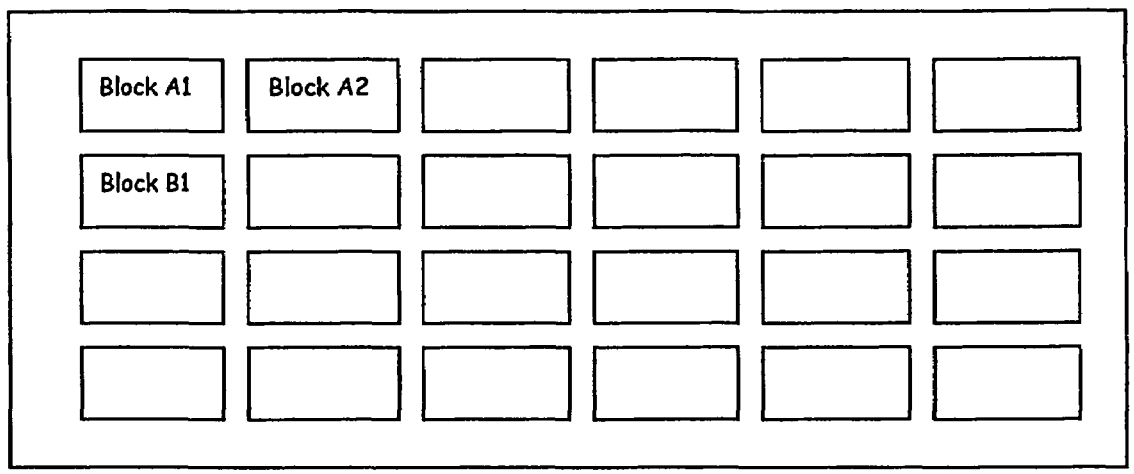
FIG. 7 illustrates one microarray slide having twenty four blocks with the left-upper corner blocks designated as Block A1, Block A2 and Block B1.

To enhance the robustness of the determination of rotational and translational offsets, and at the same time to speed up the detection process, the above steps are first performed on two blocks (e.g., top-left hand corner: Block A1 & Block A2) of the cDNA microarray slide, as shown in FIG. 7. If the rotational and translational offsets for the two blocks are identical (within a tolerance threshold T, selected by a user), the process stops. Then the offsets are taken as the final value. However, if the offset values are larger than a pre-determined threshold, then the steps will be performed for another block, e.g., block B1. The final offset values will be based on the average of the two closet sets of values, out of the 3 sets of values obtained. It is appreciated that the process may be repeated by taking additional blocks (e.g., Block B2) in the same manner for greater robustness.

Figure 8:
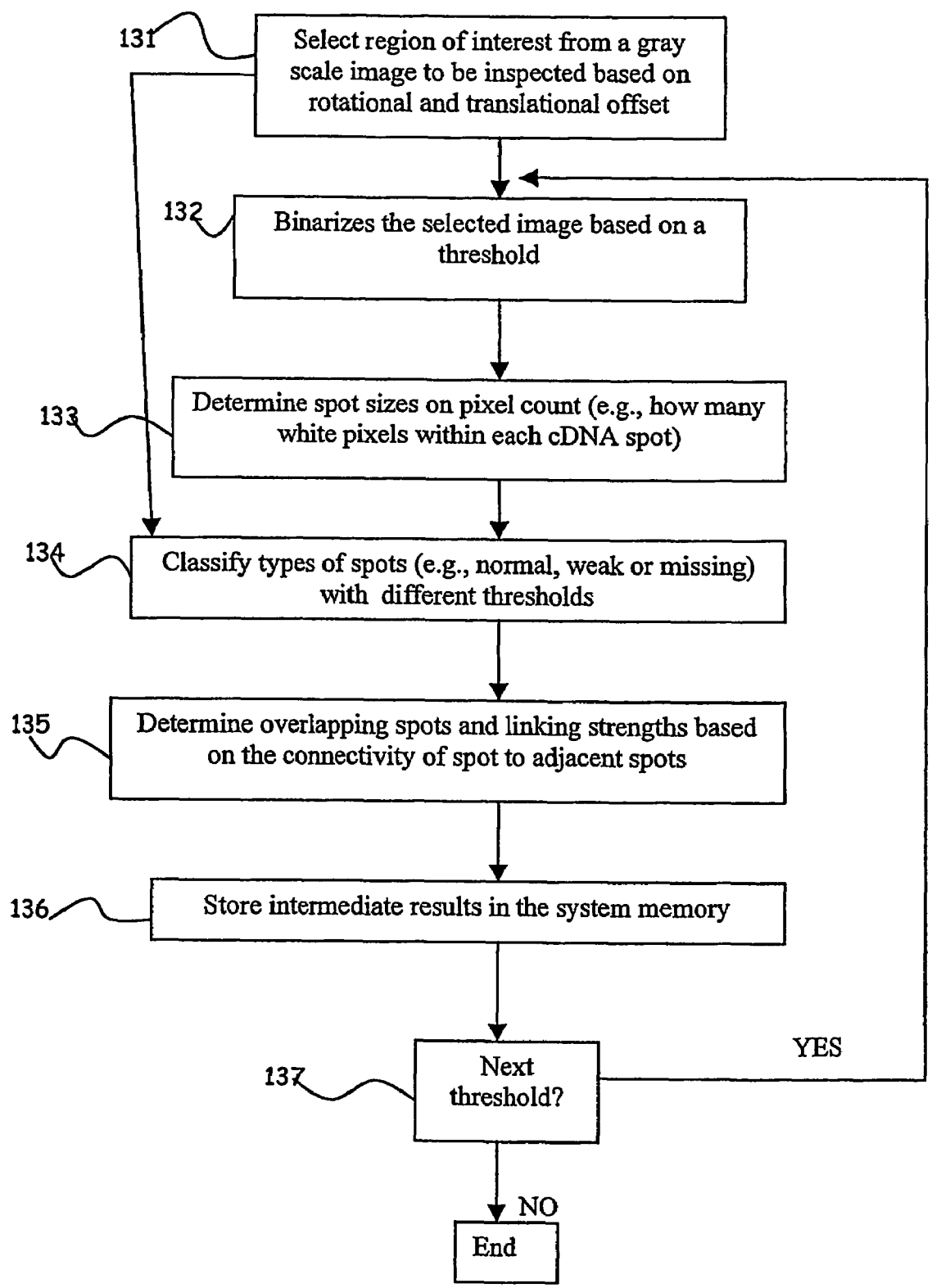
FIG. 8 is a flowchart of methods for classifying weak spots, missing spots, and overlapping spots, and determining spot sizes and linking strengths for overlapping spots.

Referring to step 130 of FIG. 3 in combination with FIG. 8, missing, weak or irregular (overlapping) spots are detected by using threshold methods. The detection uses the grayscale images that have been corrected through rotational and translational offset as discussed above. The significance of the offsets is to allow users to accurately locate the individual spots within a cDNA block. Without this step, it would not be possible to locate each spot, and one block may confuse with other cDNA blocks (due to missing spots, weak spots, overlapping spots etc.). With this step, there is no need to locate each cDNA spot using complicated algorithms or select each cDNA slide image through user via input device. Furthermore, rotational and translational offsets may be calculated by using only one or two cDNA blocks (as opposed to the entire slide), which is computationally very efficient.

Now referring to FIG. 8, one embodiment of the present invention is described for determining the weak spot, missing spot and overlapping spot, and respective linking strengths for overlapping spots. It is appreciated that it is for the sake of convenience in describing the invention step by step. There is no implication or inference that the invention has to be practiced in the described order of steps.

Referring to FIG. 8, there is provided a flowchart of methods that inspect weak spots, missing spots, overlapping spot locations on a large cDNA layout and view the inspection results on the display 31 interactively. One of the benefits for knowing that a specific spot is a missing spot, weak spot or overlapping spot is to improve the printing process for future cDNA microarray slide printing as far as possible.

Statistical data on the locations of missing spots, weak spots and overlapping spots facilitates the analysis of printing errors and their causes. For example, if a small percentage of the cDNA spots are not well printed, such spots can be identified early, and the results of this small percentage of the cDNA microarray spots can thus be excluded from further analysis. The exclusion can be realisable through the storing and subsequent retrieval of inspection results for each slide in a separate excel spread sheet. That the missing spots, weak spots and overlapping spots can be detected early and excluded from further analysis provides great saving and more accurate analysis results.

The determination of spot size is initiated by step 131 selecting the region of interest based on the rotational and translational offsets as determined by using the methods as discussed above. Then in step 132, the grayscale image of the region of interest normalized by using the rotational and translational offsets is binarized on the basis of a threshold selected by a user. Then in step 133, the size of each spot is determined on the basis of pixel count (e.g., white pixels within each cDNA spot).

The determination of whether a spot is normal, weak or missing in step 134 is also initiated by step 131 selecting the region of interest based on the rotational and translational offsets as determined by using the methods as discussed above. The missing spot is determined when the average intensity of the image intensity of the spot is below a threshold T1. The weak spot is determined when the average intensity of the image intensity of the spot is between T1 and another threshold T2 (where T2 is greater than T1). The overlapping spot is determined when the linking image intensity between spots is between T1 and another threshold T3 (where T3 is greater than T1).

Optionally, each threshold could have multiple levels. For example, if T1 has three levels, the three levels could be labelled as T1a, T1b and T1c. Similarly, T2 could have three levels such as T2a, T2b and T2c; and T3 could have T3a, T3b and T3c. The number of levels in each threshold could be determined by requirements of specific applications and computer time and capacity.

In setting up the threshold T1, T2, and T3, there are three methods that can be used. The details are given below.

First is the local threshold method which uses the average intensity of the blocks (6 or 8 blocks within the same slide) under the camera as the reference for computing T1, T2 and T3. Supposing the average intensity is Ave_1, then T1 will be a constant (called a) multiplied by Ave_1, T2 another constant (called b) multiplied by Ave_1, and T3 a third constant (called c) multiplied by Ave_1.

Second is the global threshold method which uses the average intensity of the entire microarray slide as the reference for computing T1, T2 and T3 as the local threshold method as discussed above.

Third is the universal threshold method which uses the average intensity of all the slides with the same batch as the reference for computing T1, T2 and T3 as the local threshold method as discussed above.

There are two implementation arrangements for the third method. One requires each CDNA slide to be placed twice, with the first time placement for threshold determination, and the second time for spot characteristic determination. Another requires the auto-storing of slide image in computer RAM when it is placed on the slide holder the first time for threshold determination. There is no need to place the cDNA slide on the slide holder the second time as all the pre-stored cDNA slide images will be automatically retrieved for spot characteristics determination once the threshold is determined for the entire batch of cDNA slides.

Any of the three methods can be selected to best suit specific application domains under the system setup mode.

In step 135, for the determination of overlapping spots, the linkage between two spots is directional, so that eight (8) directional linkages could be easily assigned to any linkage. The eight directional linkages include N (north), S (south), E(east), W(west), NE (north-east), NW (north-west), SE (south-east) and SW (south-west). The linking strength is determined based on image intensity and the connectivity between spots. If two spots are connected by image pixels of intensity exceeding threshold T3a, but less than threshold T3b, the linking strength is denoted as T3a. If two spots are connected by image pixels of intensity exceeding threshold T3b, but less than threshold T3c, the linking strength is denoted as T3b. If two spots are connected by image pixels of intensity values exceeding threshold T3c, the linking strength is denoted as T3c, and so on.

In step 136, all intermediate results from each determination including spot size, spot quality (normal, weak, or missing), and overlapping strength are stored in the system memory 22. In step 137, a user can set up another threshold to repeat the steps discussed above. If no more threshold is desired, step 130 will come to an end. Once the first cDNA slide is inspected, the linear slider will move to the home position, and the characteristics (weak spot, missing spot, etc. . . .) will be stored in a database (e.g., Excel i/o) (step 140). The first cDNA slide will be taken out, and a new slide will be placed on the fixture. This process will repeat itself (step 150) until all slides are inspected.

The present invention provides Excel i/o and VB6 programming for interactive display of inspection results, and a user-friendly software interface. A user-friendly interface is provided so as to facilitate the use of the low cost and reconfigurable vision inspection system. The interface includes the display of intermediate results, selection of vision algorithms, operation of linear slider, interactive display of gene data in excel spread sheet formats.

In some embodiments, a microarray slide contains pre-planned absent spots, which means that the cDNA spots at the specific locations are intentionally left empty during cDNA slide printing process. The locations of these pre-planned absent spots are given in the form of excel spread sheet with a specific format. The algorithms disclosed in the present invention make it unnecessary to look at the large excel spread sheet and the cDNA layout to work out which spot is pre-planned to be missing, and which spot is caused by printing defects.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiments chosen for illustration without departing from the spirit and scope of the invention.

Specifically, it will be apparent to one of ordinary skill in the art that the device of the present invention could be implemented in several different ways and the apparatus disclosed above is only illustrative of the preferred embodiment of the invention and is in no way a limitation. For example, it would be within the scope of the invention to vary the dimensions disclosed herein. In addition, it will be apparent that the various aspects of the above-described invention can be utilized singly or in combination with one or more of the other aspects of the invention described herein. In addition, the various elements of the present invention could be substituted with other elements.

What is claimed is:

1. A method for automatic inspection of a microarray slide, comprising one or more processors to perform the steps of:
    obtaining a gray scale image of the microarray slide, wherein the microarray slide comprises one or more blocks containing arrays of spots;
    binarizing the gray scale image by selecting a threshold;
    morphologically dilating the binarized image so as to generate a merged component;
    calculating rotational offset and translational offset of the merged component so as to align the gray scale image with a reference image;
    locating the individual spots within the arrays of spots of the microarray slide; and
    determining qualities of the located spots on the microarray slide by using threshold methods.

2. The method of claim 1, wherein the gray scale image is captured by a detection means.

3. The method of claim 2, wherein the detection means is selected from the group consisting of a charge-coupled device (CCD), a charge injection device, a photodiode array and a scanner.

4. The method of claim 3, wherein the detection means is a CCD camera.

5. The method of claim 1, wherein, in the binarization process, the threshold is predetermined by computing the histogram of the gray scale image, thereby the spots are separated from background for having intensity values exceeding the threshold.

6. The method of claim 1, wherein, in the morphological dilation process, the dilation operation uses any odd number matrix that is computational feasible.

7. The method of claim 6, wherein the matrix is a 3×3 one where the number of dilation operation is 8.

8. The method of claim 6, wherein the matrix is a 5×5 one.

9. The method of claim 6, wherein the matrix is a 7×7 one.

10. The method of claim 1, wherein the rotational offset is calculated by using any algorithms that can calculate the rotational offset of an object having a rectangular shape with a boundary.

11. The method of claim 10, wherein the rotational offset is calculated by using Sobel operation, where the magnitude of the edge of the image in the vertical direction and horizontal directions will be denoted as Gy and Gx, where Gy is determined by using Sobel Y mask of:

| −1 | −2 | −1 |
|----|----|----|
| 0  | 0  | 0  |
| 1  | 2  | 1  |

The Gx is determined by using Sobel X mask of:

| −1 | 0 | 1 |
|----|---|---|
| −2 | 0 | 2 |
| −1 | 0 | 1 |

The above edge magnitude for each image pixel is computed by computing G for each edge point by:

$$G = |Gx| + |Gy|$$

The orientation will be determined as:

$$\tan^{-1}(Gy/Gx)$$

The rotational offset is computed by getting the maximum number of edge points that give the same edge directions.

12. The method of claim 10, wherein the rotational offset is calculated by using second order moment analysis, where the central moment needs to be computed, as given in the formula below;

$$\mu_{ij} = \Sigma\Sigma(x - \text{Cen}\_x)^i (y - \text{Cen}\_y)^j P(x,y)$$

thereby the rotational offset can then be computed based on the central moments, as follows:

$$\theta = 0.5 \tan^{-1}[2\mu_{11}/(\mu_{20} - \mu_{02})].$$

13. The method of claim 1, wherein the translational offset can be calculated by any algorithms that are suitable for calculating the vertical and horizontal distances between the coordinate of one block and another reference block.

14. The method of claim 13, wherein the translational offset is calculated by using first order moment analysis, where the general moment formulation is given in the formula below:

$$M_{ij} = \Sigma\Sigma x^i y^j P(x,y)$$

where i, j are the moment indices; x is the x-coordinate of the pixel, y is the pixel's y-coordinate, and P(x,y) is the pixel's intensity; thereby the centroid X, denoted by Cen_X can be computed as:

$$\text{Cen}\_X = M_{1,0}/M_{0,0}$$

and, the centroid Y, denoted as Cen_Y can be computed as:

$$\text{Cen}\_Y = M_{0,1}/M_{0,0}$$

therefore, the determination of centroid X and centroid Y will give the translational offset.

15. The method of claim 1, wherein the qualities include spot size, spot types and overlapping strengths.

16. The method of claim 15, wherein the spot size is determined by selecting a region of interest from the gray scale image; binarizing the selected region on the basis of a threshold selected by a user; and determining the spot size on basis of pixel count.

17. The method of claim 1, wherein the types of spots include normal spots, weak spots, missing spots, and overlapping spots.

18. The method of claim 17, wherein the determination of whether a spot is normal, weak or missing comprises: selecting a region of interest from the gray scale image; establishing multi-level thresholds; and determining the type of a spot on the basis of its position in relation to the multi-level thresholds.

19. The method of claim 18, wherein the thresholds are determined by methods selected from the group consisting of local threshold method, global threshold method and universal threshold method.

20. The method of claim 17, wherein the linkage strength of the overlapping spots is determined by image intensity and the connectivity between spots, and any linkage between two spots is designated as one of the eight directional linkages: N, S, E, W, NE, NW, SE and SW.

21. The method of claim 1, wherein the microarray slide is a cDNA microarray slide.

22. A system for automatic inspection of a microarray slide, comprising:
   a keyboard for instructions/data input;
   a display for showing images;
   an image capture unit for capturing a gray scale image of the microarray slide;
   a slide holding and transporting means for delivering the microarray slide to the image capture unit for image capturing;
   a control means for controlling the operation of the slide holding and transporting means; and
   a processing unit for receiving instructions/data from the keyboard, sending image signals to the display, receiving the image data from the image capture unit, and sending controlling instructions to the control means;
   wherein the processing unit is electrically connected to the keyboard, the display, the image capture unit and the control means via separate bus lines; and
   wherein the processing unit comprises a computer-readable system memory embedded therein application programs, wherein the application programs are capable of performing:
   obtaining a gray scale image of the microarray slide, wherein the microarray slide comprises one or more blocks containing arrays of spots;
   binarizing the gray scale image by selecting a threshold;
   morphologically dilating the binarized image so as to generate a merged component;
   calculating rotational offset and translational offset of the merged component so as to align the gray scale image with a reference image;

locating the individual spots within the arrays of spots of the microarray slide; and determining qualities of the located spots on the microarray slide by using threshold methods.

23. The system of claim 22, wherein the image capture unit comprises a detection means for capturing the image of the slide, and a light source for providing the slide with illumination.

24. The system of claim 23, wherein the detection means is selected from the group consisting of a charge-coupled device (CCD), a charge injection device, a photodiode array, and a scanner.

25. The system of claim 24, wherein the detection means is a CCD camera.

26. The system of claim 23, wherein the light source is a directional frontal lighting system.

27. The system of claim 22, wherein the application programs include excel i/o database.

* * * * *